United States Patent

Steele et al.

[11] Patent Number: 5,141,869
[45] Date of Patent: Aug. 25, 1992

[54] AUTOMATED BIOLUMINESCENCE MICROBIAL MONITOR

[75] Inventors: John W. Steele, Torrington; Frederick Sribnik, Windsor, both of Conn.

[73] Assignee: United Technologies Corporation, Hartford, Conn.

[21] Appl. No.: 544,764

[22] Filed: Jun. 27, 1990

[51] Int. Cl.$^5$ .................. C12Q 1/66; C12M 1/34; A61L 2/00; G01N 21/00
[52] U.S. Cl. ................................. 435/291; 435/8; 422/58; 422/294
[58] Field of Search ............ 435/291, 8; 422/44, 422/58, 294

[56] References Cited

U.S. PATENT DOCUMENTS 3,728,227 4/1973 Elson et al. .................. 435/291
3,919,053 11/1975 Nazemi ....................... 435/291
4,687,732 8/1987 Ward et al. ..................... 435/6
4,740,467 4/1988 Kettman et al. ................. 435/7
4,833,075 5/1989 Vijayalakshmi et al. ........... 435/8

OTHER PUBLICATIONS

C. T. Gregg, Ph. D., Technical Data Notes, Los Alamos Diagnostics, Apr. 1989.
"Bioluminescence", McGraw Hill Encyclopedia of Science and Technology, vol. 2 (McGraw-Hill, 1982) pp. 268-272.

Primary Examiner—Douglas W. Robinson
Assistant Examiner—Timothy J. Reardon
Attorney, Agent, or Firm—Pamela J. Curbelo

[57] ABSTRACT

The combination of a culturing process, bioluminescence mediated by luciferin/luciferase, and a light measuring device allows microbial monitoring in liquids with microbial concentrations as low as 1 CFU/100 ml. All characteristics of this monitor are zero gravity compatible which makes it particularly suitable for applications such as monitoring microbial counts in water in a zero gravity, closed environment.

6 Claims, 1 Drawing Sheet

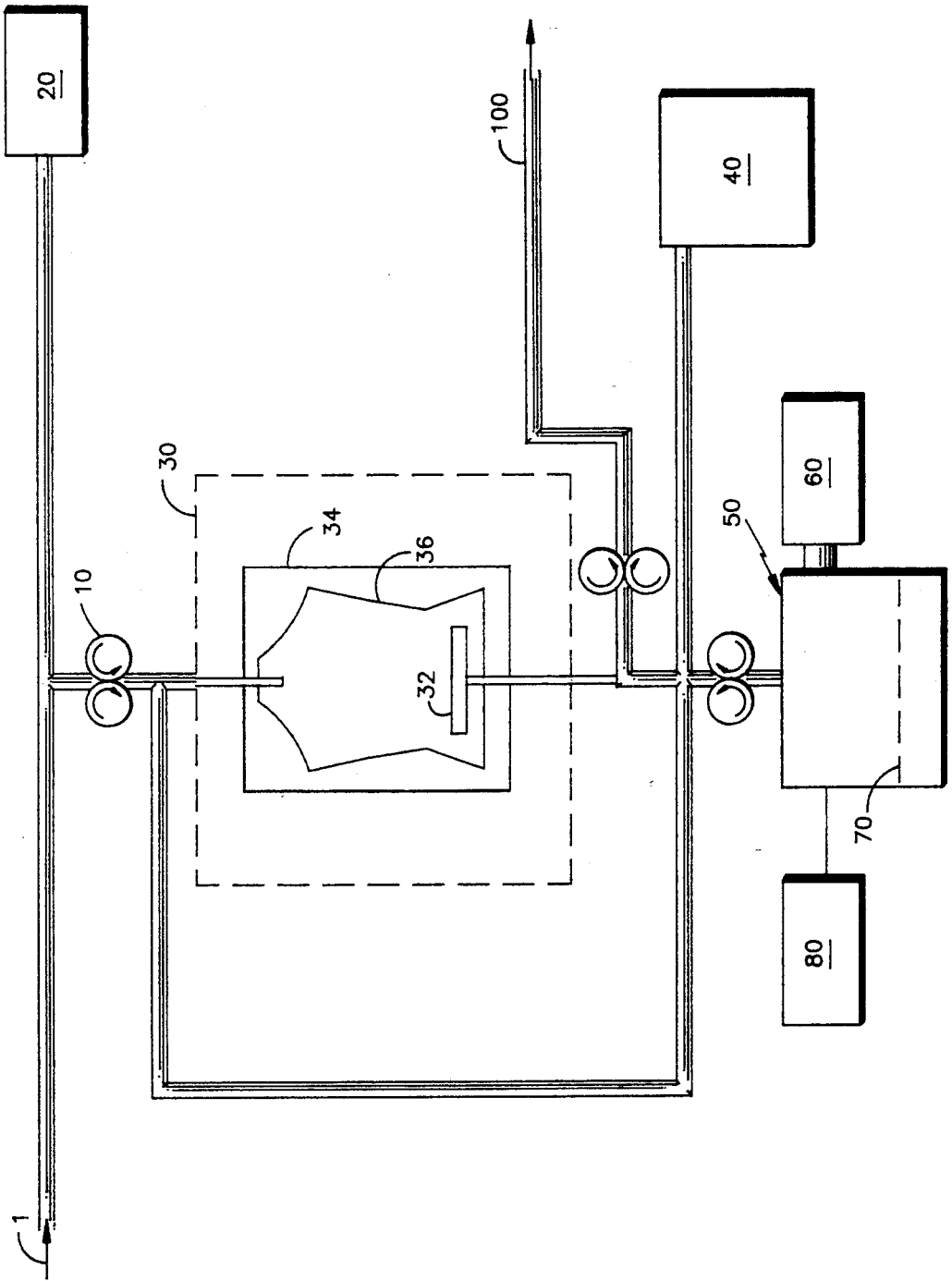

AUTOMATED BIOLUMINESCENCE MICROBIAL MONITOR

CROSS REFERENCE

This application relates to copending, U.S. patent application Ser. No. 07/544,766, for TOTAL ORGANIC HALOGEN ANALYZER, filed on Jun. 27, 1990; U.S. patent application Ser. No. 07/544,765, for AN ELUANT STORAGE AND PREPARATION APPARATUS AND METHOD FOR USING THE SAME, filed Jun. 27, 1990; U.S. patent application Ser. No. 07/544,767, for ZERO GRAVITY COMPATIBLE TOTAL ORGANIC AND INORGANIC CARBON ANALYZER, filed Jun. 27, 1990; U.S. patent application Ser. No. 07/544,763, for ZERO GRAVITY PURGE AND TRAP FOR MONITORING VOLATILE ORGANIC COMPOUNDS, filed Jun. 27, 1990 and U.S. patent application Ser. No. 07/544,768, for ZERO GRAVITY COMPATIBLE TOTAL ORGANIC AND INORGANIC CARBON ANALYZER, filed Jun. 27, 1990, all commonly assigned.

TECHNICAL FIELD

The present invention relates to a microbial monitor, and especially to an automated bioluminescence microbial monitor.

BACKGROUND ART

Microbial count in a liquid, such as water, milk, or soft drinks for human consumption and water for microelectronic and pharmaceutical product processing is of the utmost importance to health and product integrity, respectively. Microbial count analysis typically consists of a labor intensive manual membrane filtration followed by a 48 to 72 hour incubation period.

The results of the microbial analysis are interpreted by a trained analyst who visually counts the number of colonies on the filter paper after incubation. Each colony represents a single colony forming unit (CFU) in the initial sample. From this information, the number of CFUs per unit volume is determined.

Bioluminescence has been utilized by both the food industry and medical field to detect high concentrations of microbes. The detection process consists of measuring adenosine triphosphate (ATP); a nucleotide found in all living cells. ATP, the primary energy donor in viable cells, rapidly degrades as the cell dies. With the use of the enzyme luciferase (see U.S. Pat. No. 4,833,075), ATP can be measured.

ATP is released from living bacterial cells with the use of a bacterial release agent which lyses microbial cell walls. In the presence of oxygen ($O_2$), magnesium ($Mg^{++}$) and luciferase, ATP drives the conversion of luciferin to oxyluciferin. This reaction results in the conversion of ATP to adenosine monophosphate (AMP) and the release of a photon of light.

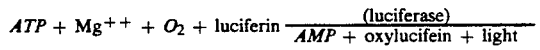

$$ATP + Mg^{++} + O_2 + luciferin \xrightarrow{\text{(luciferase)}} AMP + oxylucifein + light$$

The light can be measured by a luminometer if the concentration of microbes is about $1 \times 10^5$ CFU per milliliter (ml) or greater, the current sensitivity for the state of the art. Note, bioluminescence is typically utilized for grossly concentrated samples, not for trace level analysis.

This process is typically accomplished by sequentially adding a bacterial release agent, luciferin/luciferase, and $Mg^{++}$ to a liquid sample while a fixed luminometer records any offsets due to emitted light from the sample.

What is needed in the art is a microbial monitoring process which is automated, has high sensitivity, is zero gravity compatible, and has a decreased incubation period.

DISCLOSURE OF INVENTION

The present invention relates to a bioluminescence microbial monitor and a process for using the same. The microbial monitor is comprised of a bladder, a luciferin/luciferase assembly, a bacteria release agent reservoir, a growth buffer supply, a means for introducing a liquid sample and growth buffer to the bladder, a means for introducing an enriched sample to the luciferin/luciferase assembly, a means for mixing, and a means for measuring emitted light. The process includes enriching a liquid sample which has been introduced to the bladder, preparing an aqueous solution of luciferin/luciferase and bacteria release agent, adding some of the enriched sample to the aqueous solution, and measuring the light emitted.

The foregoing and other features and advantages of the present invention will become more apparent from the following description and accompanying drawing.

BRIEF DESCRIPTION OF DRAWINGS

The FIGURE is a schematic of one possible embodiment of the Bioluminescence Microbial Monitor of the present invention.

BEST MODE FOR CARRYING OUT THE INVENTION

This invention can be used to detect microbes, such as bacteria, in any liquid which does not degrade the detector or the chemicals used and which does not contain any other living cells such as somatic cells. The enrichment process, with the use of incubation time and sample volume as variables, allows microbe concentrations even less than 1 CFU/100 ml to be monitored.

Referring to the FIGURE, which is intended to be exemplary and not limiting, the microbial monitor of the present invention contains a sample inlet (1) and a system outlet (100), a growth buffer assembly (20), a means for metering (10), an incubation assembly (30), a bacteria release agent reservoir (40) luciferin/luciferase assembly (50), a means for measuring the light emitted (60), a means for mixing (70) and a water supply (80).

The incubation assembly (30) has a cavity (36) for containing the sample during the incubation process that can be any cavity capable of retaining the liquid sample which is flexibility enough to be contracted by pressure, such as a bladder (hereafter referred to as a bladder). An expanding bladder is useful for zero gravity operation to prevent air voids which can interfere with mixing and result in a nonhomogeneous sample. Typically, in a zero gravity environment, prior to introducing the liquid sample to the incubation assembly (30) and the bladder (36), the bladder is collapsed, containing no voids. As the liquid sample enters the bladder, the bladder (36) expands only to the size of the liquid sample, therefore preventing the formation of voids. Note, it is feasible that the incubation assembly is a bladder itself. The capacity of the bladder (36) is determined by the liquid sample size and the amount of growth buffer to be utilized. It is preferred that the bladder capacity be equivalent to the amount of liquid sample/growth buffer mixture preventing possible gas voids.

Within the bladder (36) is a bacteria filter (32) to initially concentrate the liquid sample. The bacteria filter (32), which can be any filter commonly known in the art, must have a pore size small enough to trap the microbes yet large enough to allow liquid permeation. Since a typical microbe ranges in size from about 0.50 to about 1.0 micron, a pore size less than about 0.50 microns can be used. The preferred pore size is between about 0.10 and about 0.45 microns, with between about 0.18 to about 0.25 microns especially preferred.

The collection process consists of passing sufficient liquid into the bladder (36) in the incubation assembly (30). The majority of the liquid is passed through the bacteria filter (32) to allow for initial concentration, leaving only sufficient liquid to incubate any CFUs (trapped by the bacteria filter (32)) retained in the incubation assembly (30). Preferably, 100 ml of liquid is injected into the incubation assembly (30) for simplicity purposes. Generally, 90 ml pass through the bacteria filter (32) and 10 ml are retained in the bladder (36) for the enrichment process (hereafter referred to as the liquid sample).

Once the liquid sample has been filtered, it is enriched. Enrichment is accomplished by adding growth buffer to the liquid sample. Any broth or buffer, commonly known in the art, which does not contain a source of ATP and which enhances microbial growth can be used as a growth buffer. One such growth buffer is sterile Hepes® solution produced by Los Alamos Inc., Los Alamos, N. Mex.

Although mixing and heating are not necessary, the growth buffer and the liquid sample are mixed and heated to accelerate the enrichment process. Mixing, which helps prevent dead zones of no mixing and temperature hot spots, which and helps achieve intimate contact, can be any means conventionally known in the art. If the apparatus is to be utilized in a zero gravity environment, it must be capable of zero gravity operation (hereafter referred to as zero gravity compatible). One convenient, zero gravity compatible mixing process is pulsating pressure applied to the exterior surface of the bladder (36). Nonreactive gas pulsed on the exterior surface of the bladder (36) causes mixing. Nonreactive gases such as helium, argon, nitrogen, and air, among others, can be used if they do not significantly permeate the bladder material or impact the process. Heating helps to accelerate the enrichment process. The heating can be accomplished by any means conventionally known in the art, such as enclosing the incubation assembly (30) with a furnace or oven (34).

The time period for enrichment is a function of the generation time for the organism and the liquid sample volume. For example, common water borne organisms have a typical incubation period of about 20 minutes. As a result, a 1 CFU/100 ml liquid sample can be enriched to approximately $2 \times 10^6$ to $3 \times 10^6$ CFU/ml within six hours.

After enrichment, the enriched sample is added to an aqueous solution. The aqueous solution is prepared by adding water, from the water supply (80) preferably deionized water, and bacteria release agent from the bacteria release agent reservoir (40) to the luciferin/luciferase in the luciferin/luciferase assembly (50). The luciferin/luciferase can be obtained from Los Alamos Diagnostics Inc., Los Alamos, N. Mex. in a premixed, freeze dried form. It is also possible to purchase luciferin and luciferase separately and combine them at a ratio which can readily be determined by an artisan.

For example, when testing a water liquid sample in a zero gravity, closed environment, 1.0 ml of water is added to 3.0 ml of bacteria release agent and 250 mg luciferin/luciferase solid. The bacteria release agent can be any enzyme mix or extracting reagent which lyses cells to release cellular ATP and inhibits enzymatic activity in the extract, such as Picoex B ™ produced by Los Alamos Diagnostics Inc., Los Alamos, N. Mex.

To ensure contact between the luciferin/luciferase and to prevent gas voids, a means for providing pressure, such as a cuvette assembly which is spring loaded, can be used.

To attain a homogeneous mixture, the luciferin/luciferase, water, and bacteria release agent are mixed. Any means for mixing (70), such as a vibrator assembly, ultrasonic blender, mixer, or any other means for mixing conventionally known in the art which is zero gravity compatible, can be used.

Once the aqueous solution is prepared and the enrichment process is complete, some of the enriched sample is added to the aqueous solution at a ratio between approximately 1:15 to approximately 1:17 respectively, with a ratio of 1:16 preferred.

The enriched sample/aqueous solution mixture is mixed until homogeneous, approximately 5.0 seconds. Light readings are taken until the reaction has gone to completion, typically approximately 30 seconds. Any means for measuring light (photons) conventionally known in the art can be utilized, such as a luminometer (60) or photometer. Note, the light can be transferred from the luciferin/luciferase assembly (50) to the luminometer (60) by any means conventionally known in the art which will not contaminate the enriched sample/aqueous solution mixture or the light itself, such as fiber optics or a window connected to a tube.

After the analysis is complete, the growth buffer assembly (20), incubation assembly (30), and the means for providing pressure are replaced either manually or by an automated carousel. These components can be discarded or reclaimed by cleaning, autoclaving, and recharging. Note, all remaining components should be sterilized, such as by heat, prior to subsequent analysis procedures to prevent contamination.

EXAMPLE

The following procedure can be used to obtain a microbial count in potentially potable water.

1. 100 milliliters (ml) of sample water is released into the bladder (36) (see the FIGURE) within the incubation assembly (30).

2. 90 ml of the sample passes through the bacteria filter (32), for initial concentration while 10 ml of the sample is retained in the bladder (36), creating a 10:1 concentration. The last 20 ml of sample water to pass through the bladder (36) is expelled with controlled nitrogen (N₂) pressurization on the exterior surface of the bladder (36) within the incubation assembly (30).

3. 20 ml of growth buffer, sterile Hepes solution, is then added to the bladder (36).

4. N₂ pressure pulsing is used to mix the growth buffer and sample for 2.0 minutes.

5. The enrichment period within the fully expanded bladder (36) is 6 hours at 95° F.

6. After enrichment, a retractable needle is used to deliver 1.0 ml of deionized water and 3.0 ml of bacteria release agent, Picoex B, into the spring loaded cuvette assembly containing 250 mg of luciferin/luciferase.

7. A fixed sample vibrator mixes the contents of the cuvette assembly.

8. 250 microliters of enriched sample is removed from the bladder (36) via a retractable needle, metered into the cuvette assembly, and mixed with the fixed sample vibrator.

9. Luminescence readings are then taken of the light emitted with a fixed luminometer.

Unlike the prior art, the present invention is automated, can test very low microbial count samples, can be operated in zero gravity, and requires a shorter incubation period than the prior art. Note, the shorter incubation period is attributed to the sensitivity of the process with respect to the sensitivity of the human eye. In order to visually count the number of colonies on the filter paper, an incubation period of between 48 to 72 hours is required. The present invention only requires an incubation period of between about 1 and about 7 hours, while the entire analysis process only requires between about 1.5 and about 7.5 hours if 1 CFU/100 ml sensitivity is desired. Note, shorter periods are feasible, depending upon the sensitivity of the luminometer, the generation period for the microbe, and the liquid sample volume.

Although this invention has been shown and described with respect to detailed embodiments thereof, it will be understood by those skilled in the art that various changes in form and detail thereof may be made without departing from the spirit and scope of the claimed invention.

We claim:

1. A microbial monitor, which comprises:
   a. a bladder for enriching microbial concentration in a liquid sample constructed so as to expand to a volume commensurate with a volume of said liquid sample and a volume of growth buffer introduced to said bladder, wherein said construction enables zero gravity compatibility;
   b. a means in flow communication with said bladder for introducing the liquid sample to said bladder;
   c. a second means in flow communication with said bladder for introducing the growth buffer to said bladder;
   d. a bacteria filter located within said blader for concentrating the amount of microbes in the liquid sample, wherein said concentrated microbes grow in said growth buffer to become enriched in concentration;
   e. a luciferin/luciferase assembly in flow communication with said bladder for containing luciferin/luciferase and for receiving bacteria release agent and a sample of said enriched microbial concentration from said bladder;
   f. a bacteria release agent reservoir in flow communication with said luciferin/luciferase assembly, for supplying the bacteria release agent to said luciferin/luciferase assembly;
   g. a means for mixing the luciferin/luciferase with the bacteria release agent and the enriched microbial concentration thereby causing the emission of light; and
   h. a means for measuring said emitted light, wherein said means for measuring said emitted light is connected to said luciferin/luciferase assembly.

2. A microbial monitor as in claim 1 wherein said liquid sample is selected from the group consisting of water, milk, soft drinks, and urine.

3. A microbial monitor as in claim 1 wherein said means for measuring light emitted is selected from the group consisting of a luminometer and a photometer.

4. A microbial monitor as in claim 1 further comprising a means for heating the liquid sample and the growth buffer in said bladder.

5. A microbial monitor as in claim 4 wherein said means for heating is selected from the group consisting of a furnace and an oven.

6. A microbial monitor as in claim 1, further comprising a water supply flow communication with said luciferin/luciferase assembly for supplying water to said luciferin/luciferase assembly, wherein the water is mixed with the luciferin/luciferase, the bacteria release agent, and the enriched microbial concentration.

* * * * *

UNITED STATES PATENT AND TRADEMARK OFFICE
CERTIFICATE OF CORRECTION

PATENT NO.  : 5,141,869

DATED       : August 25, 1992

INVENTOR(S) : John W. Steele et al

It is certified that error appears in the above-identified patent and that said Letters Patent is hereby corrected as shown below:

Column 3, line 39, "which and helps" should be --and which helps--.

Signed and Sealed this

Twenty-fourth Day of August, 1993

Attest:

Attesting Officer

BRUCE LEHMAN

Commissioner of Patents and Trademarks